US007318338B2

United States Patent
Moisio et al.

(10) Patent No.: US 7,318,338 B2
(45) Date of Patent: Jan. 15, 2008

(54) MEASURING DEVICE FOR MEASURING AEROSOL

(75) Inventors: Mikko Moisio, Tampere (FI); Risto Luoma, Tampere (FI); Kimmo Pietarinen, Tampere (FI); Leo Holma, Kangasala (FI); Marko Palonen, Tampere (FI)

(73) Assignee: Dekati Oy, Tampere (FI)

( * ) Notice: Subject to any disclaimer, the term of this patent is extended or adjusted under 35 U.S.C. 154(b) by 21 days.

(21) Appl. No.: 10/496,085

(22) PCT Filed: Nov. 20, 2002

(86) PCT No.: PCT/FI02/00924

§ 371 (c)(1),
(2), (4) Date: Oct. 25, 2004

(87) PCT Pub. No.: WO03/044492

PCT Pub. Date: May 30, 2003

(65) Prior Publication Data
US 2005/0039517 A1    Feb. 24, 2005

(30) Foreign Application Priority Data
Nov. 21, 2001   (FI) .................................. 20012259

(51) Int. Cl.
*G01N 7/00*     (2006.01)
(52) U.S. Cl. ................. 73/28.05; 73/863.22; 73/23.33; 324/71.4
(58) Field of Classification Search ............... 73/28.01, 73/28.04, 28.05, 865.5, 863.22, 23.33; 324/71.4
See application file for complete search history.

(56) References Cited

U.S. PATENT DOCUMENTS

| 2,702,471 | A | * | 2/1955 | Vonnegut .................... 73/28.01 |
| 3,153,577 | A | * | 10/1964 | McCully et al. .............. 422/98 |
| 3,413,545 | A |   | 11/1968 | Whitby |
| 3,473,118 | A | * | 10/1969 | Herceg et al. ............... 324/722 |
| 3,561,253 | A | * | 2/1971 | Dorman ..................... 73/24.03 |
| 3,718,029 | A |   | 2/1973 | Gourdine et al. |
| 3,879,986 | A | * | 4/1975 | Sehmel ....................... 73/28.04 |
| 4,140,005 | A | * | 2/1979 | Kittelson ................... 73/28.02 |
| 4,171,341 | A | * | 10/1979 | Morgan ........................ 422/98 |
| 4,294,105 | A | * | 10/1981 | Kelly ........................ 73/28.01 |
| 4,656,832 | A | * | 4/1987 | Yukihisa et al. .............. 60/303 |
| 5,008,628 | A | * | 4/1991 | Krigmont et al. ........... 324/693 |

(Continued)

FOREIGN PATENT DOCUMENTS

DE          19824744 A1     3/1999

(Continued)

*Primary Examiner*—Michael Cygan
(74) *Attorney, Agent, or Firm*—Venable LLP; Eric J. Franklin

(57) ABSTRACT

The invention relates to a measuring device for measuring aerosols, which measuring device comprises detection means (13), means (41) for conveying a signal from the detection means (13), a first insulation (43), a second insulation (44), and a supporting means (42). The first insulation (43) insulates the medium (41) from the supporting means (42), and the second insulation (44) insulates the detection means (13) from the supporting means (42). Also, the second insulation (44) is designed in such a way that it positions the detection means (13) in a predetermined location.

9 Claims, 3 Drawing Sheets

U.S. PATENT DOCUMENTS

Figure 3:
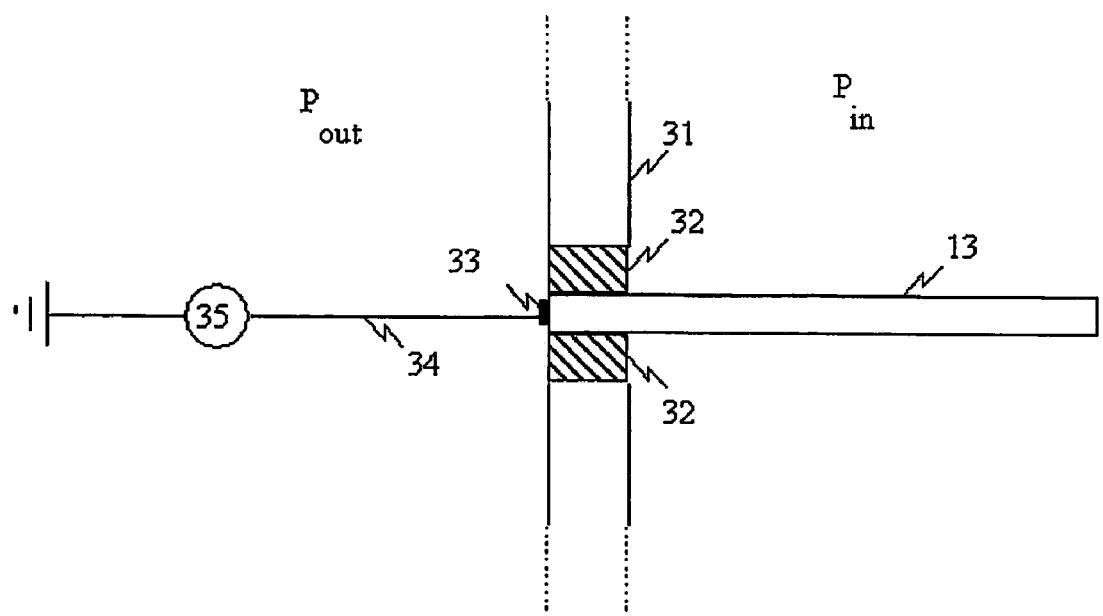

| | | | |
|---|---|---|---|
| 5,247,827 A * | 9/1993 | Shah | 73/28.01 |
| 6,192,740 B1 * | 2/2001 | Thomas et al. | 73/28.01 |
| 6,965,240 B1 * | 11/2005 | Litton et al. | 324/464 |
| 2001/0035044 A1 * | 11/2001 | Larsson et al. | 73/28.01 |

FOREIGN PATENT DOCUMENTS

| | | |
|---|---|---|
| SU | 524107 A | 10/1976 |
| SU | 842894 A | 7/1981 |
| WO | WO8404390 A1 | 11/1984 |

* cited by examiner

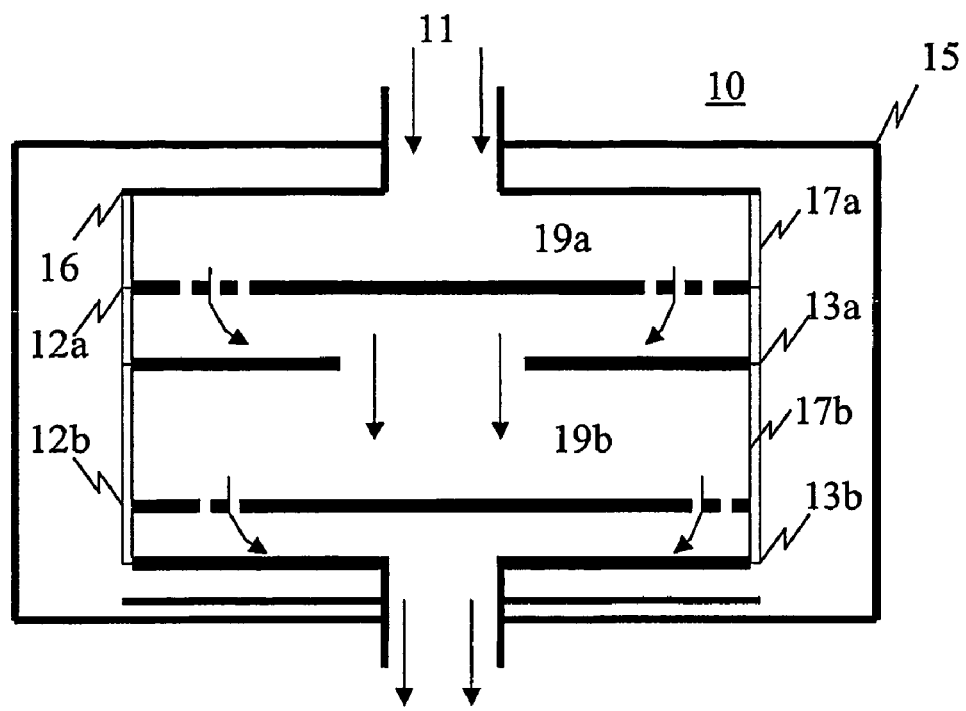
Fig. 1 *Prior Art*
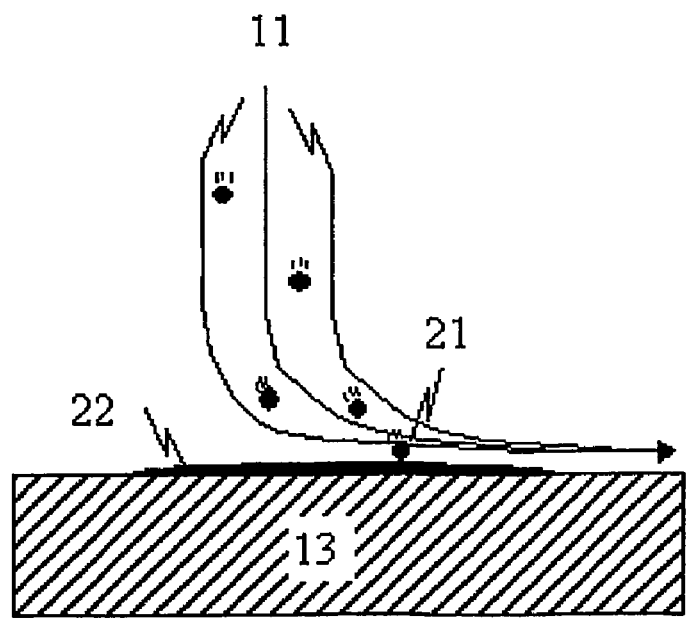
Fig. 2 *Prior Art*

MEASURING DEVICE FOR MEASURING AEROSOL

The invention relates to a measuring device according to the preamble of claim 1.

With tightening environmental regulations, there is an increasing need for the measurement of particle emissions. In particular, the need for measurement is present in the development of filtering methods, in the research of various combustion processes, as well as in processes for monitoring actual emissions. In particle measurements, so-called cascade impactors have been conventionally used to classify the particles according to the particle size.

FIG. 1 shows a cross-sectional view of an impactor 10 consisting of several stages according to prior art. To simplify the figure, only the two first stages have been drawn. The flow 11 to be analyzed is sucked, for example by negative pressure, through the impactor 10. The air flow 11 is introduced through the frame structure 15 of the impactor to a first chamber 19a. Each stage comprises a nozzle part 12a; 12b equipped with orifices which are passed through by the flow carrying particles. Collection surfaces 13a; 13b are placed behind the nozzle parts 12a; 12b. The collection surface is provided with at least one outlet, through which the flow is allowed to flow to the next chamber or out of the impactor.

FIG. 2 shows a detail of the collection surface 13. The flow direction of the air flow 11 through the orifices of the nozzle part is abruptly changed when it impacts upon the collection surface 13. Particles 21 carried by the flow 11 and having a sufficiently low mechanical mobility cannot follow the abrupt change in the direction of the flow but they hit the collection surface 13. The particles 21 having hit the collection surface 13 are deposited on the collection surface 13, forming a mass 22.

The mechanical mobility of the particles depends in a known way on the particle size. This makes it possible to classify the particles selectively according to the size. By selecting, in a known way, the number and size of orifices in the nozzle part 12a, 12b shown in FIG. 1, the distance between the nozzle part 12a; 12b and the collection surface 13a; 13b, as well as the flow rate to be used, it is possible to dimension each impactor stage in such a way that only particles having a mechanical mobility smaller than a desired value, i.e. being larger than a given particle size, are deposited on the collection surface 13a; 13b at each stage.

The successive stages can be dimensioned so that the first stage collects the largest particles (for example, particles with a diameter greater than 100 μm), the second stage collects the particles slightly smaller than these (for example, 10 to 100 μm), and the next stages would collect smaller and smaller particles, respectively. Thus, by measuring the masses 22 deposited on the collection surfaces 13 of the different collecting stages, it is possible to determine the size distribution of the particles in the flow under analysis. In electrical impactors, an estimate of the mass deposited on the collection surface is made by monitoring the current caused by electric charges discharged by particles deposited on the collection surface. In arrangements of prior art, the collection surface is electrically coupled to an ammeter outside the impactor. To implement this electrical connection, the impactor must have been provided with an electrical lead-through.

FIG. 3 shows an electrical lead-through of prior art. In FIG. 3, the collection plate 13 is insulated from the rest of the impactor structure 31 by means of insulations 32. The collecting plate is coupled by means of a connector 33 to an electric conductor 34, via which the current is led to the ammeter 35 for detection. Because the pressure $P_{in}$ in the inner parts of the impactor deviates from the pressure $P_{out}$ outside the impactor, the joint between the insulations 32 and the frame part 31 of the impactor must be pressure-sealed; otherwise, the measurements may be affected by an undesirable extra flow in the joint.

On the other hand, it must be possible to install the collection surface 13 relatively precisely, particularly in relation to the nozzle part in front of it, because the size distribution of the particles deposited on the collection surface depends e.g. on the distance between the nozzle part and the collection surface, as stated above. Thus, tolerances in the placement of the collection surface are directly reflected in the reliability of the measurements to be made by the impactor.

A problem involved in the above-described lead-through of prior art is that the insulations 32 are subjected to three different requirements. The joint formed should insulate the collection surface 13 from the other parts 31 of the impactor, position the collection surface 13 at a predetermined point, and be pressure-tight. Of these, particularly the two last mentioned requirements are contradictory. A good positioning structure requires mechanical rigidity, but a good pressure-tight joint is best achieved by slightly elastic materials. Consequently, the lead-through of prior art is thus, even in the best case, a compromise between the various contradictory demands.

Another problem in the arrangement of prior art is piezoelectric and tripoelectric phenomena occurring in many insulations, such as Teflon, when they are subjected to mechanical stress. For this reason, these insulations may, when subjected to mechanical stress, cause disturbances in exactly the same electric signals which they should insulate from external noise. To achieve a pressure-tight joint, the frame structure 31 of the impactor should be tightly compressed against the insulation 32. Thus, the insulation 31 is subjected not only to the mechanical stress caused by the pressure difference but also to the compression caused by the frame part 31.

The aim of the measuring device disclosed in this application is to eliminate the above-described problems of prior art. In the measuring device according to the invention, said contradictory requirements are taken care of with different insulation units. One insulation unit will be responsible for the pressure sealing of the joint, and the other for the positioning of the collection surface. In this way, it is possible to implement a measuring device to provide a more precise positioning of the collection surface in the measuring device than in the arrangement of prior art, which is reflected as improved reliability of the results obtained with the measuring device.

Furthermore, the measuring device according to the invention has the advantage to the measuring device of prior art that it is smaller and its parts are easier to clean and replace.

The measuring device according to the invention is characterized in what will be presented in the characterizing part of claim 1.

Figure 4:
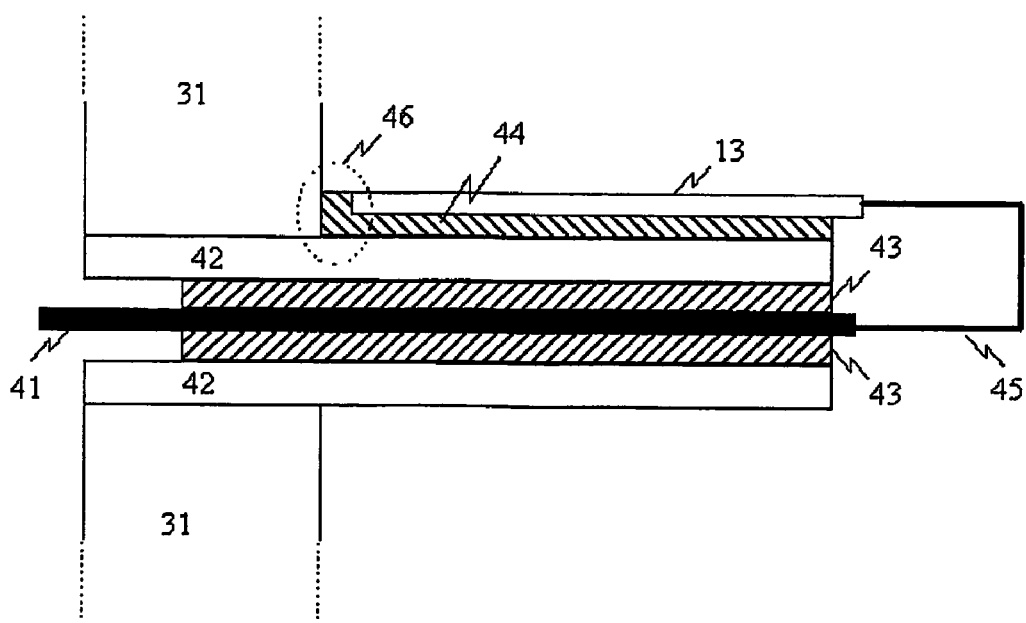
Figure 5:
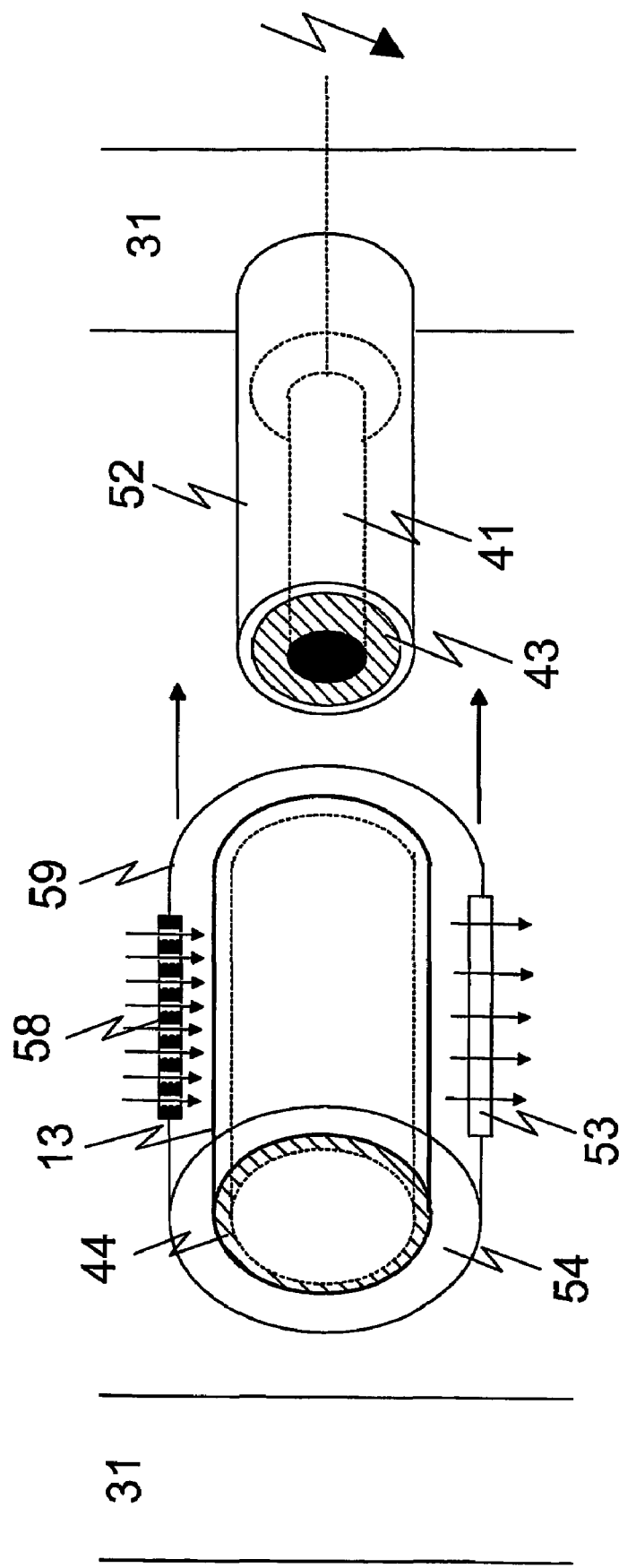

In the following, the invention will be described in detail with reference to the appended drawings, in which FIG. 1 shows an impactor of prior art, FIG. 2 shows the impingement of particles to be measured on a collection surface, FIG. 3 shows a lead-through of prior art, FIG. 4 shows other embodiments of the measuring device according to the invention, and FIG. 5 shows another embodiment of the measuring device according to the invention.

FIGS. 1, 2 and 3 have been discussed above in connection with the prior art.

In the following, preferred embodiments of the invention will be described. The arrangement according to the invention can be preferably used in an electrical low pressure impactor, but the basic idea of the invention can also be utilized in other kinds of aerosol measuring devices.

Similarly, in the following, reference will be made to a collection surface as the element detecting the particles, but in view of the basic idea of the invention, it is not significant, what kind of an element is used for detecting the particles.

In the present application, to facilitate the understanding of the matter, the term particle is primarily used instead of the terms aerosol or aerosol particle. However, the intention is not to restrict the term particle to refer to solid particles only, but it also refers to minor quantities of substances in other phases, such as, for example, aerosol particles. The term aerosol is defined as an assembly of liquid or solid particles suspended in a gaseous medium.

FIG. 4 shows an embodiment of the measuring device according to the invention. The frame part 31 is provided with a lead-through for discharging a measuring signal from the measuring device. A conductor 41 made of a suitable medium passes through the lead-through to carry the signal. Depending on the form of the signal, the conductor may be, for example, an electric wire, if the signal is an electrical signal, or a photoconductor, if the signal is a light signal.

Preferably, a mechanically rigid supporting means 42 is also installed in connection with the lead-through. The supporting means 42 is insulated from the conductor 41 by means of a first insulator 43. The joint formed by the first insulator 43 between the conductor 41 and the supporting means 42 is preferably pressure-tight. Said joint does not need to be a positioning one, which allows for more implementation alternatives than the arrangement of prior art.

The mechanical stresses on the frame part 31 of the measuring device, such as the compression stress caused by the assembly of the measuring device, are preferably focused on the rigid supporting means 42, wherein they cannot be focused on the insulations 43 and 44. Thanks to this, the arrangement of the invention reduces piezoelectric or tripoelectric disturbances compared with the arrangement of prior art.

The conductor 41 is preferably arranged to convey information about the material deposited on the collection surface 13. In its simplest form, the arrangement consists of an electrical coupling arranged between the collecting surface 13 and the conductor 41, preferably by means of an electric wire 45. More complicated structures may also include means capable of sophisticated signal processing between the collection surface 13 and the conductor 41. For example, it is possible to couple electronic components between them to amplify the electric signal, or electro-optical converters to convert the electrical signal to a light signal.

A second insulation 44 has been installed between the collection surface 13 and the supporting means 42. The second insulation 44 is used to prevent the electrical coupling of the collection plate 13 with the supporting means 42 and thereby the frame part 31 of the device. If necessary, the second insulation 44 can be designed preferably in such a way that it also insulates the collection surface 13 directly from the frame part 31 of the measuring device and possibly from other parts of the measuring device. In FIG. 4, the second insulation 44 is designed in the above-mentioned way. The protrusion 46 of the second insulation 44 extends between the collecting surface 13 and the frame part 31 of the device. The insulation of the collecting surface and the other parts of the device does not need to be implemented with the same insulation as the insulation between the collection surface 13 and the supporting means 42, but the insulation can, if necessary, be also implemented with a separate insulation (not drawn in the figure).

The second insulation 44 is preferably designed in such a way that it positions the collection surface 13 in a predetermined location. The location of the collection surface 13 is preferably such that the size distribution of the particles deposited on the collection plate is known, either by a theoretical analysis or by a previously performed calibration. Because it is necessary to disassemble and reassemble the measuring device from time to time, the supporting means 42, the second insulation 44 and the collection surface 13 are preferably made such that they can be easily disassembled and reassembled so that the collection plate 13 can be repeatedly positioned in the same location as precisely as possible. The collection surface 13 may preferably consist of, for example, a thin material to be installed on top of the second insulation 44. If the supporting means is rotationally symmetrical, such as a pipe, the second insulation 44 can also be implemented to be rotationally symmetrical and the collection surface to be a thin film placed on top of the second insulation 44.

In view of the above-mentioned positioning, it is advantageous that the means involved in the positioning are mechanically as rigid as possible, and the mechanical stress on them is as low as possible, respectively. The pressure-tight joint is subjected to the mechanical stress. This mechanical stress is typically smaller than the mechanical stress transmitted by the frame part. In the arrangement according to the invention, the mechanical stress caused by the pressure difference is focused on the joint formed by the first insulation 43. In the solution according to the invention, the second insulation 44 does not form a pressure-tight joint; consequently, it or the collecting plate 13 are not subjected to a significant mechanical stress, which allows a better positioning than in the arrangement of prior art. Furthermore, the device is easier to disassemble and reassemble than devices of prior art, because there is no need to arrange the positioning and the pressure-tightness at the same time.

In FIG. 4, the supporting means 42 is illustrated as a separate element, but the supporting means 42 can also be integrated in the frame structure of the measuring device, as exemplified in the embodiment of FIG. 5 below. The frame structure of the measuring device may also be used as the supporting means as such, wherein a separate supporting means will not be needed. Irrespective of the way of implementing the supporting means 42, it is advantageous that the supporting means forms a mechanically rigid joint with the other parts of the measuring device. Mechanical rigidity is desirable, because the second insulation 44 positions the collection surface preferably in relation to the supporting means 42, wherein the accuracy of the positioning of the collection surface 13 in relation to the other parts of the device depends on the positioning of the supporting means 42. In the arrangement according to the invention, the positioning of the supporting means can be implemented without an electrical insulation between the supporting means 42 and the frame part 31 of the device. Thus, the joint can be implemented, for example, by providing the supporting means 42 and its counter surface with matching threadings.

FIG. 5 shows another embodiment of the arrangement according to the invention. In the figure, the cylindrical supporting means 52 is preferably integrated in the frame part 31 of the measuring device. As described above, the conductor 41 and the first insulation 43 are installed inside the supporting means 52. In the figure, the second insulation 44, the collection surface 13 and a nozzle part 58 are connected to a separate connecting element 59. Thus, for example one stage of the impactor could be formed simply by sliding the connecting element 59 onto the supporting means 52. The rigidity of such a structure can be further increased by supporting the connecting element 59 to at least one another supporting structure in addition to the supporting means 52. Preferably, this could be implemented by supporting one end 54 of the connecting element to the frame part 31 of the measuring device, on the opposite side of the measuring device when seen from the supporting means 52. The arrangement of FIG. 5 has the advantage that the nozzle part 58 and the collection plate 13, which are essential for the size distribution of the particles to be deposited on the stage, form a part of the same unit, whereby their tolerances are better under control, which is manifested by increasing the reliability of the device.

The connecting element 59 can also be implemented in such a way that the second insulation 44 and the collection surface 13 can be removed from the connecting element 59 and, if desired, be placed around the supporting part 52 without the connecting element 59.

The geometric design of the lead-through or the collection surface is not essential for the invention. The design can be implemented according to the requirements of each measuring device or measuring situation. The lead-through and the collection plate can be preferably cylindrical, as shown in FIG. 5, but if desired, the collection surface can be, for example, plate-like, as in conventional impactors.

Hereinabove, some embodiments of the measuring device according to the invention have been described, but the invention is not restricted solely to these embodiments, but it can vary within the scope of the appended claims.

The invention claimed is:

1. A measuring device for measuring aerosol, comprising:
   at least one nozzle part;
   at least one detector downstream of the at least one nozzle part, wherein said detector is a collection surface;
   a frame part enclosing said at least one nozzle part and said at least one detector;
   a signal medium for conveying information from said detector, wherein said detector and said signal medium are in an electrical contact with each other;
   a support connected to said frame part;
   a first insulation operative to insulate said detector from said support; and
   a second insulation operative to insulate said detector from said support, wherein said second insulation has such a profile that said detector is set in a predetermined position in relation to said nozzle part.

2. The measuring device according to claim 1, wherein said information is information about material deposited on said collection surface.

3. The measuring device according to claim 1, wherein said measuring device is an electrical low pressure impactor.

4. The measuring device according to claim 1, wherein the insulation formed between said first insulation and said support is pressure-tight and unpositioned.

5. The measuring device according to claim 1, wherein said second insulation also insulates said detector from the other parts of said measuring device.

6. The measuring device according to claim 1, wherein said support is integrated in said frame part.

7. The measuring device according to claim 1, further comprising:
   a connecting element comprising said detector.

8. The measuring device according to claim 1, further comprising:
   a connecting element comprising a nozzle part.

9. The measuring device according to claim 1, further comprising:
   a connecting element comprising said second insulation.

* * * * *